(12) United States Patent
Iimura et al.

(10) Patent No.: US 7,378,425 B2
(45) Date of Patent: May 27, 2008

(54) (1-INDANONE)-(1,2,3,6-TETRAHYDROPYRIDINE) COMPOUNDS

(75) Inventors: Yoichi Iimura, Ibaraki (JP); Takashi Kosasa, Ibaraki (JP); Yoshiharu Yamanishi, Ibaraki (JP)

(73) Assignee: Eisai R & D Management Co., Ltd., Bunkyo-ku (JP)

( * ) Notice: Subject to any disclaimer, the term of this patent is extended or adjusted under 35 U.S.C. 154(b) by 545 days.

(21) Appl. No.: 10/940,747

(22) Filed: Sep. 15, 2004

(65) Prior Publication Data

US 2005/0124642 A1 Jun. 9, 2005

Related U.S. Application Data

(63) Continuation-in-part of application No. PCT/JP03/03630, filed on Mar. 25, 2003.

(30) Foreign Application Priority Data

Mar. 29, 2002 (JP) .............................. 2002-095352

(51) Int. Cl.
C07D 211/70 (2006.01)
A61K 31/44 (2006.01)
(52) U.S. Cl. ..................................... 514/277; 546/340
(58) Field of Classification Search ................ 546/340; 514/277
See application file for complete search history.

(56) References Cited

U.S. PATENT DOCUMENTS 4,895,841 A   1/1990   Sugimoto et al.

FOREIGN PATENT DOCUMENTS

| EP | 0296560 A2 | 12/1988 |
|---|---|---|
| JP | 5-505172 A | 8/1993 |
| JP | 6-329535 A | 11/1994 |
| JP | 7-89949 A | 4/1995 |
| JP | 9-508893 A | 9/1997 |
| JP | 2733203 B2 | 12/1997 |
| JP | 11-503140 A | 3/1999 |
| JP | 11-34981 A | 12/1999 |
| JP | 2000-319257 A | 11/2000 |
| JP | 2000-319258 A | 11/2000 |
| JP | 2001-139547 A | 5/2001 |
| WO | WO-91/03243 A1 | 3/1991 |
| WO | WO-95/15948 A1 | 6/1995 |
| WO | WO-96/31208 A2 | 10/1996 |

OTHER PUBLICATIONS

Kato et al. "TAK-147, an acetylcholinesterase inhibitor, increases choline acetyltransferase activity in cultured rat septal cholinergic neurons", Neuroscience Letters, vol. 260, pp. 5-8, 1999.
Walker et al. "Sigma receptors: biology and function", Pharmacological Reviews, vol. 42, No. 4, pp. 355-402, 1990.
Folia Pharmacol. Jpn., vol. 114, pp. 3-11, 1999.
Gilligan et al. "Piperidinyltetralin o Ligands", J. Med. Chem., Vo. 37, pp. 364-370, 1994.

*Primary Examiner*—Zinna N. Davis
(74) *Attorney, Agent, or Firm*—Birch, Stewart, Kolasch & Birch, LLP

(57) ABSTRACT

The present invention provides an excellent sigma receptor binding agent and/or acetylcholinesterase inhibitor containing an (1-indanone)-(1,2,3,6-tetrahydropyridine) compound. More specifically, it provides an (1-indanone)-(1,2,3,6-tetrahydropyridine) compound represented by the following formula, a pharmacologically acceptable salt thereof or a hydrate thereof:

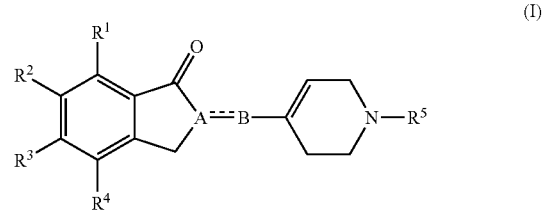

In the formula (I), $R^1$, $R^2$, $R^3$ and $R^4$ are the same as or different from each other.

30 Claims, No Drawings

(1-INDANONE)-(1,2,3,6-TETRAHYDROPYRIDINE) COMPOUNDS

This application is a Continuation-In-Part of co-pending Application No. PCT/JP03/03630 filed on Mar. 25, 2003, the entire contents of which are hereby incorporated by reference and for which priority is claimed under 35 U.S.C. § 120. This application also claims priority under 35 U.S.C. § 119(a) on Patent Application No. 2002-95352 filed in Japan on Mar. 29, 2002. The entire content of each of the above documents is hereby incorporated by reference.

TECHNICAL FIELD

The present invention relates to an (1-indanone)-(1,2,3,6-tetrahydropyridine) derivative, and a sigma receptor binding agent and/or acetylcholinesterase inhibitor containing the (1-indanone)-(1,2,3,6-tetrahydropyridine) derivative.

PRIOR ART

Most of antipsychotic drugs and agents for treating schizophrenia conventionally clinically used are dopamine receptor antagonists. However, most of these antipsychotic drugs and agents for treating schizophrenia, such as haloperidol that is approved as effective in clinical use, show adverse drug actions such as extrapyramidal symptoms due to their dopamine receptor blocking action.

Recent studies have indicated that ligands and receptors belonging to non-dopaminergic mechanisms, such as serotonin, phencyclidine, muscarinic acetylcholine and sigma receptors, are also involved in mental disorders.

Among them, the sigma receptors were proposed as a subtype of opiate receptors that are combined typically with morphine to thereby induce hallucination by Martin et al., 1976. However, subsequent studies revealed that the sigma receptors are non-opiate receptors and that multitude of antipsychotic drugs and agents for treating schizophrenic disorder, such as haloperidol, have high affinity for the sigma receptors. Thus, compounds capable of binding to the sigma receptors have received attention as candidates for agents for treating schizophrenic disorder (Pharmacol. Reviews, 42, 355(1990)). Further studies on the sigma receptors have reported that compounds capable of binding to sigma receptors have a variety of actions, in addition to antipsychotic action, neuroprotection, antidepressant, anxiolytic, antidementia, anticonvulsive, drug dependency antagonistic, antiussive, stegnotic, anti-inflammatory, lacrimal fluid protein-release stimulating, and central micturition reflex depressant actions (Folia Pharmacol. Japon, 114, 3(1999)).

Examples of compounds having a sigma receptor binding action can be found as 1-cycloalkylpiperidines, antipsychotic drugs, disclosed in JP-A 5-505172; sigma receptor antagonists disclosed in JP-A 6-329535; 1,4-(diphenylalkyl) piperazine derivatives disclosed in JP-A 7-89974; 2-arylalkenylazacycloalkane derivatives disclosed in JP-A 9-508893; and use for production of agents for treatment of a sigma-receptor-modulated disease disclosed in JP-A 11-503140.

J. Med. Chem., 37, 364(1994) and Neuroscience Lett., 260, 5(1999) disclose that 1-benzyl-4-[(5,6-dimethoxy-1-indanon)-2-yl]methylpiperidine, known as an acetylcholinesterase inhibitor, has a sigma receptor binding action. JP-A 11-349481 discloses that 1-benzyl-4-(5,6-dimethoxy-1-indanon)-2-yl]piperidine has a sigma receptor binding action.

The present inventors have reported the following compounds ((1) to (4)) as compounds having an acetylcholinesterase inhibitory action.

(1) A cyclic amine derivative represented by the following formula, a pharmacologically acceptable salt thereof or a hydrate of them.

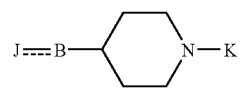

Wherein J is, for example, the formula:

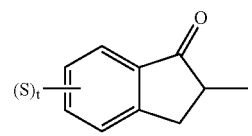

(wherein S is, for example, a lower alkoxy group having one to six carbon atoms; and t is 0 or an integer of 1 to 4); B is, for example, methylene chain; K is, for example, a benzyl group which may be substituted; and the partial structure:

```
=====
``` is a single bond or double bond, provided that a compound wherein J is 5,6-dimethoxy-1-indanon-2-yl group; B is —$CH_2$— group; and K is unsubstituted benzyl group, a pharmacologically acceptable salt thereof or a hydrate of them are excluded (JP-B2 2733203).

(2) A compound represented by the following formula:

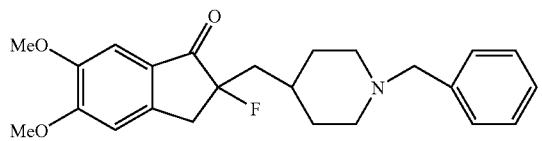

or a pharmacologically acceptable salt thereof (JP-A 2000-319257).

(3) A 4-substituted piperidine derivative fluoride represented by the following formula:

(wherein $R^1$ is, for example, a substituent represented by:

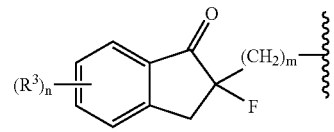

(wherein $R^3$s are the same as or different from each other and each represents, for example, an alkoxy group having one to six carbon atoms; m is 0 or an integer of 1 to 6; and n is an integer of 1 to 4); and $R^2$ is, for example, a benzyl group which may be substituted, provided that 1-benzyl-4-[(5,6-dimethoxy-2-fluoro-1-indanon)-2-yl]methylpiperidine or a pharmacologically acceptable salt thereof is excluded), a pharmacologically acceptable salt thereof or a hydrate of them (JP-A 2000-319258).

(4) A 4-substituted piperidine derivative represented by the following formula:

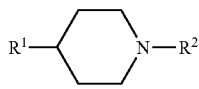

(wherein $R^1$ is, for example, a group represented by the formula:

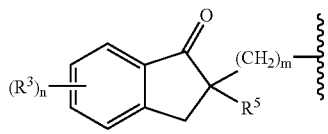

(wherein $R^3$s are the same as or different from each other and each represents, for example, an alkoxy group having one to six carbon atoms; $R^5$ is, for example, a halogen atom except for fluorine atom; m is 0 or an integer of 1 to 6; and n is an integer of 1 to 4); and $R^2$ is, for example, benzyl group which may be substituted), a pharmacologically acceptable salt or a hydrate of them (JP-A 2001-139547).

However, the relationship between these compounds and the sigma receptors has not yet been known.

As is described above, compounds having a sigma receptor binding action are promising agents for treating various diseases, but conventional sigma receptor binding agents are now under development, and agents highly clinically usable have not yet been found. Therefore, demands have been made to provide sigma receptor binding agents having well-balanced efficacy and safety.

DISCLOSURE OF THE INVENTION

After intensive investigations to provide compounds and sigma receptor binding agents satisfying the above requirements, the present inventors have found that novel indanone derivatives have an outstanding sigma receptor binding action, are useful as sigma receptor binding agents and are also useful as acetylcholinesterase inhibitors. The present invention has been accomplished based on these findings.

Specifically, the present invention relates to:

1) an (1-indanone)-(1,2,3,6-tetrahydropyridine) compound represented by the formula:

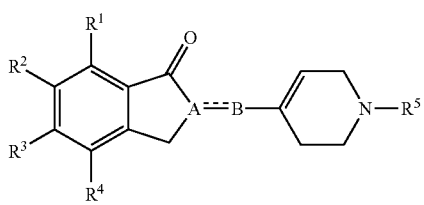

(in the formula (I), $R^1$, $R^2$, $R^3$ and $R^4$ are the same as or different from each other and each represents a group selected from hydrogen atom, a halogen atom, hydroxyl group, nitrile group, an alkyl group having one to six carbon atoms which may be substituted, a cycloalkyl group having three to eight carbon atoms which may be substituted, an alkoxy group having one to six carbon atoms which may be substituted, a cycloalkoxy group having three to eight carbon atoms which may be substituted, an acyl group having one to six carbon atoms which may be substituted, an $C_1$-$C_6$ alkoxy-carbonyl group which may be substituted, an $C_1$-$C_6$ alkyl-aminocarbonyloxy group which may be substituted, a di-($C_1$-$C_6$ alkyl)-aminocarbonyloxy group which may be substituted, nitro group, an amino group which may be substituted, an amide group which may be substituted, mercapto group and a thioalkoxy group having one to six carbon atoms which may be substituted, where $R^1$ and $R^2$, or $R^2$ and $R^3$, or $R^3$ and $R^4$ may together form an aliphatic ring, an aromatic ring, a heterocyclic ring or an alkylenedioxy ring; the partial structure:

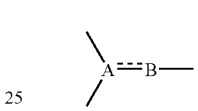

is a group represented by >C=CH—(CH$_2$)$_m$— or >C(R$^6$)—CH(R$^6$)—(CH$_2$)$_m$— (wherein m is 0 or an integer from 1 to 5; and $R^6$ is hydrogen atom, a halogen atom, hydroxyl group, an alkyl group having one to six carbon atoms, an alkoxy group having one to six carbon atoms, nitrile group, a haloalkyl group having one to six carbon atoms, a hydroxyalkyl group having one to six carbon atoms, a cyano-$C_1$-$C_6$ alkyl group, an aminoalkyl group having one to six carbon atoms, nitro group, azide group, an amino group which may be substituted, carbamoyl group which may be substituted, carboxyl group which may be substituted, mercapto group or a thioalkoxy group having one to six carbon atoms); and $R^5$ is hydrogen atom, an alkyl group having one to six carbon atoms which may be substituted, an alkenyl group having two to six carbon atoms which may be substituted, an alkynyl group having two to six carbon atoms which may be substituted, a cycloalkyl group having three to eight carbon atoms which may be substituted, an 2,2-(alkylenedioxy) ethyl group or a group represented by the formula:

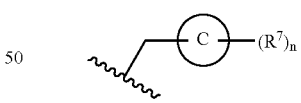

(wherein the ring C is benzene ring, an aliphatic ring or a heterocyclic ring; $R^7$s are the same as or different from each other and each represents hydrogen atom, a halogen atom, hydroxyl group, nitrile group, an alkyl group having one to six carbon atoms which may be substituted, an alkenyl group having two to six carbon atoms which may be substituted, an alkynyl group having two to six carbon atoms which may be substituted, a cycloalkyl group having three to eight carbon atoms which may be substituted, an alkoxy group having one to six carbon atoms which may be substituted, an $C_1$-$C_6$ alkoxy-alkoxy group which may be substituted, an aryloxy group which may be substituted, an aralkyloxy group which may be substituted or the like, where two of $R^7$s may together form an aliphatic ring, an aromatic ring, a heterocyclic ring or an alkylenedioxy ring; and n is an integer from 1 to 5)), a pharmacologically acceptable salt thereof or a hydrate of them;

2) the (1-indanone)-(1,2,3,6-tetrahydropyridine) compound described in 1), a pharmacologically acceptable salt thereof or a hydrate of them, wherein $R^1$ and $R^4$ are hydrogen atoms; and $R^2$ and $R^3$ are the same as or different from each other and each represents hydrogen atom, a halogen atom, an alkyl group having one to six carbon atoms which may be substituted, a cycloalkyl group having three to eight carbon atoms which may be substituted, an alkoxy group having one to six carbon atoms which may be substituted or a cycloalkoxy group having three to eight carbon atoms which may be substituted, or $R^2$ and $R^3$ may together form an aliphatic ring, an aromatic ring, a heterocyclic ring or an alkylenedioxy ring;

3) the (1-indanone)-(1,2,3,6-tetrahydropyridine) compound described in 1) or 2), a pharmacologically acceptable salt thereof or a hydrate of them, wherein $R^6$ is hydrogen atom, a halogen atom or an alkyl group having one to six carbon atoms;

4) the (1-indanone)-(1,2,3,6-tetrahydropyridine) compound described in any one of 1) to 3), a pharmacologically acceptable salt thereof or a hydrate of them, wherein $R^5$ is a group represented by the formula:

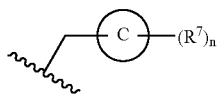

wherein the ring C, $R^7$ and n have the same meanings as defined above;

5) the (1-indanone)-(1,2,3,6-tetrahydropyridine) compound described in 4), a pharmacologically acceptable salt thereof or a hydrate of them, wherein the ring C is benzene ring or a cycloalkyl ring having three to eight carbon atoms;

6) the (1-indanone)-(1,2,3,6-tetrahydropyridine) compound described in 4), a pharmacologically acceptable salt thereof or a hydrate of them, wherein $R^7$s are the same as or different from each other and each represents hydrogen atom, a halogen atom, an alkyl group having one to six carbon atoms which may be substituted, an alkenyl group having two to six carbon atoms which may be substituted, an alkynyl group having two to six carbon atoms which may be substituted, a cycloalkyl group having three to eight carbon atoms which may be substituted, or two of $R^7$s may together form an aliphatic ring, an aromatic ring, a heterocyclic ring or an alkylenedioxy ring;

7) the (1-indanone)-(1,2,3,6-tetrahydropyridine) compound described in 4), a pharmacologically acceptable salt thereof or a hydrate of them, wherein n is an integer of 1 or 2;

8) the (1-indanone)-(1,2,3,6-tetrahydropyridine) compound described in any one of 1) to 7), a pharmacologically acceptable salt thereof or a hydrate of them, wherein the partial structure:

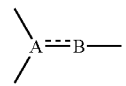

is a group represented by $>C(R^6)-CH(R^6)-(CH_2)_m-$ (wherein m is 0 or an integer from 1 to 5; and $R^6$ is hydrogen atom);

9) the (1-indanone)-(1,2,3,6-tetrahydropyridine) compound described in any one of 1) to 7), a pharmacologically acceptable salt thereof or a hydrate of them, wherein the partial structure:

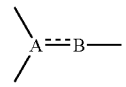

is a group represented by $>C(R^6)-CH(R^6)-(CH_2)_m-$ (wherein m is 0 or an integer from 1 to 5; and $R^6$ is a halogen atom, hydroxyl group, an alkyl group having one to six carbon atoms, an alkoxy group having one to six carbon atoms, nitrile group, a haloalkyl group having one to six carbon atoms, a hydroxyalkyl group having one to six carbon atoms, a cyano-$C_1$-$C_6$ alkyl group, an aminoalkyl group having one to six carbon atoms, nitro group, azide group, an amino group which may be substituted, carbamoyl group which may be substituted, carboxyl group which may be substituted, mercapto group or a thioalkoxy group having one to six carbon atoms;

10) the (1-indanone)-(1,2,3,6-tetrahydropyridine) compound described in 1), a pharmacologically acceptable salt thereof or a hydrate of them, wherein the (1-indanone)-(1,2,3,6-tetrahydropyridine) compound represented by the formula (I) is one selected from:
(1) 1-benzyl-4-[(5,6-dimethoxy-1-indanon)-2-yl]methyl-1,2,3,6-tetrahydropyridine,
(2) 1-benzyl-4-[(5,6-diethoxy-1-indanon)-2-yl]methyl-1,2,3,6-tetrahydropyridine, and
(3) 1-benzyl-4-[(5,6-diethoxy-2-fluoro-1-indanon)-2-yl]methyl-1,2,3,6-tetrahydropyridine;

11) a pharmaceutical composition comprising the (1-indanone)-(1,2,3,6-tetrahydropyridine) compound described in any one of 1) to 10), a pharmacologically acceptable salt thereof or a hydrate of them;

12) the pharmaceutical composition described in 11), which is a sigma receptor binding agent;

13) the pharmaceutical composition described in 11), which is a sigma receptor antagonist or a sigma receptor agonist;

14) the pharmaceutical composition described in 11), which is an agent for preventing, treating and/or improving a disease against which a sigma receptor-active drug is efficacious;

15) the pharmaceutical composition described in 11), which is an agent for preventing, treating and/or improving a disease against which a sigma receptor antagonistic action is efficacious;

16) the pharmaceutical composition described in 11), which is an agent for preventing, treating and/or improving a disease against which a sigma receptor agonistic action is efficacious;

17) the pharmaceutical composition described in 11), which is an agent for preventing, treating and/or improving a mental disorder;

18) the pharmaceutical composition described in 17), wherein the mental disorder is at least one selected from a disorder accompanied with cerebrovascular dementia and/or senile dementia, a schizophrenic disorder, an emotional disturbance, a depression, a neurosis, a psychophysiologic disorder and an anxiety disorder;

19) the pharmaceutical composition described in 18), wherein the disorder accompanied with cerebrovascular dementia and/or senile dementia is at least one selected from aggressive behavior, mental excitement, wandering, delirium, hallucination and hyperkinesis;

20) the pharmaceutical composition described in 11), which is an agent for improving intellectual function;

21) the pharmaceutical composition described in 11), which is an acetylcholinesterase inhibitor;

22) the pharmaceutical composition described in 11), which is an agent for preventing, treating and/or improving senile dementia, cerebrovascular dementia, an attention-deficit hyperactive disorder, glaucoma, myasthenia gravis and/or migraine;

23) the pharmaceutical composition described 21), wherein the senile dementia is an Alzheimer-type dementia;

24) a method for preparing the (1-indanone)-(1,2,3,6-tetrahydropyridine) compound of 8), a pharmacologically acceptable salt thereof or a hydrate of them, which comprises reducing an (1-indanone)-pyridinium compound represented by the formula:

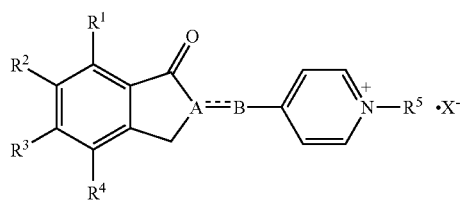

(II)

(in the formula (II), $R^1$, $R^2$, $R^3$ and $R^4$ are the same as or different from each other and each represents a group selected from hydrogen atom, a halogen atom, hydroxyl group, nitrile group, an alkyl group having one to six carbon atoms which may be substituted, a cycloalkyl group having three to eight carbon atoms which may be substituted, an alkoxy group having one to six carbon atoms which may be substituted, a cycloalkoxy group having three to eight carbon atoms which may be substituted, an acyl group having one to six carbon atoms which may be substituted, an $C_1$-$C_6$ alkoxy-carbonyl group which may be substituted, an $C_1$-$C_6$ alkyl-aminocarbonyloxy group which may be substituted, a di-($C_1$-$C_6$ alkyl)-aminocarbonyloxy group which may be substituted, nitro group, an amino group which may be substituted, an amide group which may be substituted, mercapto group and a thioalkoxy group having one to six carbon atoms which may be substituted, where $R^1$ and $R^2$, or $R^2$ and $R^3$, or $R^3$ and $R^4$ may together form an aliphatic ring, an aromatic ring, a heterocyclic ring or an alkylenedioxy ring; the partial structure:

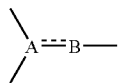

is a group represented by $>C=CH-(CH_2)_m-$ or $>C(R^6)-CH(R^6)-(CH_2)_m-$ (wherein m is 0 or an integer from 1 to 5; and $R^6$ is hydrogen atom); and $R^5$ is hydrogen atom, an alkyl group having one to six carbon atoms which may be substituted, an alkenyl group having two to six carbon atoms which may be substituted, an alkynyl group having two to six carbon atoms which may be substituted, a cycloalkyl group having three to eight carbon atoms which may be substituted, an 2,2-(alkylenedioxy)ethyl group or a group represented by the formula:

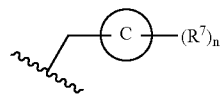

(wherein the ring C is benzene ring, an aliphatic ring or a heterocyclic ring; $R^7$s are the same as or different from each other and each represents hydrogen atom, a halogen atom, hydroxyl group, nitrile group, an alkyl group having one to six carbon atoms which may be substituted, an alkenyl group having two to six carbon atoms which may be substituted, an alkynyl group having two to six carbon atoms which may be substituted, a cycloalkyl group having three to eight carbon atoms which may be substituted, an alkoxy group having one to six carbon atoms which may be substituted, an $C_1$-$C_6$ alkoxy-alkoxy group which may be substituted, an aryloxy group which may be substituted, an aralkyloxy group which may be substituted or the like, where two of $R^7$s may together form an aliphatic ring, an aromatic ring, a heterocyclic ring or an alkylenedioxy ring; and n is an integer from 1 to 5.)), a pharmacologically acceptable salt thereof or a hydrate of them with a reducing agent and oxidizing the reduced product with an oxidizing agent;

25) the method for preparing the (1-indanone)-(1,2,3,6-tetrahydropyridine) compound, a pharmacologically acceptable salt thereof or a hydrate of them described in 24), wherein the reducing agent is sodium borohydride, and wherein the oxidizing agent is manganese dioxide, a chromium oxidizing agent or a Swern oxidizing agent;

26) a method for preparing the (1-indanone)-(1,2,3,6-tetrahydropyridine) compound of 9), a pharmacologically acceptable salt thereof or a hydrate of them, which comprises allowing the (1-indanone)-(1,2,3,6-tetrahydropyridine) compound of 8), a pharmacologically acceptable salt thereof or a hydrate of them to react with a base, and subjecting the reaction product to an electrophilic reaction with an electrophilic reagent;

27) the method for preparing the (1-indanone)-(1,2,3,6-tetrahydropyridine), a pharmacologically acceptable salt thereof or a hydrate of them described in 26), wherein the base is lithium diisopropylamide (LDA) or lithium bis(trimethylsilyl)amide;

28) the method for preparing the (1-indanone)-(1,2,3,6-tetrahydropyridine), a pharmacologically acceptable salt thereof or a hydrate of them described in 26), wherein the electrophilic reagent is N-chlorosuccinimide, N-bromosuccinimide, N-iodosuccinimide, (10-camphorsulfonyl)oxaziridine, iodomethane or sodium azide;

29) the method for preparing the (1-indanone)-(1,2,3,6-tetrahydropyridine), a pharmacologically acceptable salt thereof or a hydrate of them described in any one of 26) to 28), wherein the electrophilic reagent is a fluorinating agent;

30) the method for preparing the (1-indanone)-(1,2,3,6-tetrahydropyridine), a pharmacologically acceptable salt thereof or a hydrate of them described in 29), wherein the fluorinating agent is N-fluorobenzenesulfonimide, 3-cyclohexyl-2-fluoro-2,3-dihydro-3-methyl-1,1-dioxido-1,2-benzisothiazole, 2-fluoro-3,3-dimethyl-2,3-dihydro-1,2-benzisothiazole-1,1-dioxide, diethylaminosulfur trifluoride, N,N-diethyl-1,1,2,3,3,3-hexafluoropropylamine, hydrogen fluoride, a tetraalkylammonium fluoride, potassium fluoride, cesium fluoride or hydrogen fluoride-pyridine;

31) a method for preventing, treating and/or improving a disease against which a sigma receptor binding action and/or an acetylcholinesterase inhibitory action is efficacious, which comprises administering to a subject a pharmacologically effective amount of the (1-indanone)-(1,2,3,6-tetrahydropyridine) compound of any one of 1) to 10), a pharmacologically acceptable salt thereof or a hydrate of them; and 32) use of the (1-indanone)-(1,2,3,6-tetrahydropyridine) compound of any one of 1) to 10), a pharmacologically acceptable salt thereof or a hydrate of them, for producing an agent for preventing, treating and/or improving a disease against which a sigma receptor binding action and/or an acetylcholinesterase inhibitory action is efficacious.

The symbols, terms and other descriptions as used herein will be explained, and the present invention will be illustrated in detail below.

The "halogen atom" as used in the formula (1) refers to, for example, fluorine atom, chlorine atom, bromine atom and iodine atom, of which fluorine atom, chlorine atom and bromine atom are preferred.

The "$C_{1-6}$ alkyl group" in the formula (I) means an alkyl group having one to six carbon atoms, and preferred examples are a linear or branched alkyl group such as methyl group, ethyl group, n-propyl group, i-propyl group, n-butyl group, i-butyl group, t-butyl group, n-pentyl group, i-pentyl group, neopentyl group, hexyl group, 1-methylpropyl group, 1-ethylpropyl group, 1-methylbutyl group or 2-methylbutyl group, of which methyl group, ethyl group, n-propyl group, i-propyl group, 2-methyl-1-propyl group and t-butyl group are more preferred.

The term "cycloalkyl group having three to eight carbon atoms" in the formula (I) means a cyclic alkyl group having three to eight carbon atoms, and preferred examples are cyclopropyl group, cyclobutyl group, cyclopentyl group, cyclohexyl group, cycloheptyl group and cyclooctyl group.

The "$C_{1-6}$ alkoxy group" in the formula (I) is preferably a linear or branched alkoxy group such as methoxy group, ethoxy group, n-propoxy group, i-propoxy group, n-butoxy group, i-butoxy group, t-butoxy group, pentyloxy group or hexyloxy group. Preferred examples of the "substituent" in the "$C_{1-6}$ alkoxy group which may be substituted" are hydroxyl group, a halogen atom, nitrile group and nitro group.

The "cycloalkoxy group having three to eight carbon atoms" in the formula (I) is preferably cyclopropoxy group, cyclobutoxy group, cyclopentyloxy group, cyclohexyloxy group, cycloheptyloxy group or cyclooctyloxy group, of which cyclopentyloxy group, cyclohexyloxy group, cycloheptyloxy group and cyclooctyloxy group are more preferred.

The "$C_{1-6}$ acyl group" in the formula (I) means a linear or branched acyl group derived from a fatty acid having one to six carbon atoms, and, for example, formyl group, acetyl group, propionyl group, butyryl group, isobutyryl group, valeryl group, isovaleryl group, pivaloyl group and hexanoyl group are preferred.

A suitable "$C_{1-6}$ alkoxy-carbonyl group" in the formula (I) is methoxycarbonyl group, ethoxycarbonyl group, n-propoxycarbonyl group, i-propoxycarbonyl group, n-butoxycarbonyl group, i-butoxycarbonyl group, tert-butoxycarbonyl group, pentyloxycarbonyl group or hexyloxycarbonyl group, of which methoxycarbonyl group, ethoxycarbonyl group, n-propoxycarbonyl group and i-propoxycarbonyl group are more preferred.

Suitable examples of the "$C_{1-6}$ alkyl-aminocarbonyloxy group" and "di ($C_{1-6}$ alkyl)-aminocarbonyloxy group" in the formula (I) are methylaminocarbonyloxy group, ethylaminocarbonyloxy group, n-propylaminocarbonyloxy group, i-propylaminocarbonyloxy group, n-butylaminocarbonyloxy group, i-butylaminocarbonyloxy group, tert-butylaminocarbonyloxy group, n-pentylaminocarbonyloxy group, i-pentylaminocarbonyloxy group, neopentylaminocarbonyloxy group, hexylaminocarbonyloxy group, 1-methylpropylaminocarbonyloxy group, 1-methylbutylaminocarbonyloxy group, 2-methylbutylaminocarbonyloxy group, dimethylaminocarbonyloxy group, diethylaminocarbonyloxy group, di-(n-propyl)-aminocarbonyloxy group, di-(i-propyl)-aminocarbonyloxy group, di-(n-butyl)-aminocarbonyloxy group, di-(i-butyl)-aminocarbonyloxy group, di-(tert-butyl)-aminocarbonyloxy group, di-(n-pentyl)-aminocarbonyloxy group, di-(i-pentyl)-aminocarbonyloxy group, di-(neopentyl)-aminocarbonyloxy group, di-(n-hexyl)-aminocarbonyloxy group, di-(1-methylpropyl)-aminocarbonyloxy group, di-(1-methylbutyl)-aminocarbonyloxy group and di-(2-methylbutyl)-aminocarbonyloxy group.

The "amino group which may be substituted" in the formula (I) means an amino group whose nitrogen atom may be substituted with, for example, an alkyl group having one to six carbon atoms or sulfonic acid residue, and the "amino group" also includes a cyclic amino group. Examples of the "amino group which may be substituted" include amino group, methylamino group, dimethylamino group, pyrrolidinyl group, pyrazolinyl group, piperidyl group, piperazinyl group, acetamide group, propionamide group, methanesulfonamide group, ethanesulfonamide group, toluenesulfonamide group and N-methylacetamide group.

The "amide group which may be substituted" in the formula (I) means an amide group which may be substituted with a group such as an alkyl group having one to six carbon atoms. The amide group herein also includes an amide group of a cyclic amine. Examples of the "amide group which may be substituted" are amide group, N-methylamide group, N,N-dimethylamide group, N-ethylamide group, N,N-diethylamide group, N-methyl-N-ethylamide group, pyrrolidinylcarbonyl group, pyrazolinylcarbonyl group, piperidylcarbonyl group and piperazinylcarbonyl group.

The "thio-$C_{1-6}$ alkoxy group" in the formula (I) means sulfur atom combined with a group having the same meaning as in the definition of the "$C_{1-6}$ alkyl group" and includes, for example, methylthio group ($—SCH_3$) or ethylthio group ($—SC_2H_5$).

In the formula (I), the "aliphatic ring" is not specifically limited, but is preferably cyclopentane ring, cyclohexane ring, cycloheptane ring or cyclooctane ring. A preferred "aromatic ring" is, for example, furan ring, thiophene ring, pyrrole ring, imidazole ring, oxazole ring, thiazole ring, triazole ring, pyridine ring, pyrazine ring or pyrimidine ring.

A preferred example in the case when "R$^1$ with R$^2$, or R$^2$ with R$^3$, or R$^3$ with R$^4$ together form an alkylenedioxy ring" is methylenedioxy group, ethylenedioxy group or propylenedioxy group.

In the formula (I), the repetition number m is preferably 0 or an integer of 1 to 5, more preferably 0 or an integer of 1 to 3, further preferably 0 or an integer of 1 or 2, and most preferably 0 or 1. The repetition number n is preferably an integer of 1 to 5.

The "C$_{2-6}$ alkenyl group" in the formula (I) means an alkenyl group having two to six carbon atoms and includes a linear or branched alkenyl group having two to six carbon atoms, such as vinyl group, allyl group, 1-propenyl group, isopropenyl group, 1-buten-1-yl group, 1-buten-2-yl group, 1-buten-3-yl group, 2-buten-1-yl group or 2-buten-2-yl group, of which vinyl group, allyl group and isopropenyl group are preferred.

The "C$_{2-6}$ alkynyl group" in the formula (I) means an alkynyl group derived from an alkyne having two to six carbon atoms. A suitable group is a linear or branched alkynyl group having two to six carbon atoms, such as ethynyl group, 1-propynyl group, 2-propynyl group, butynyl group, pentynyl group or hexynyl group.

The "2,2-(alkylenedioxy)ethyl group" in the formula (I) means a group (acetal group) corresponding to ethyl group except with a cyclic alkylenedioxy group replacing terminal carbon atoms thereof. A preferred group is 2,2-(ethylenedioxy)ethyl group (also called as (1,3-dioxolan-2-yl)methyl group), 2,2-(propylenedioxy)ethyl group (also called as (1,3-dioxan-2-yl)methyl group) or 2,2-(butylenedioxy)ethyl group (also called as (1,3-dioxepan-2-yl)methyl group), of which 2,2-(ethylenedioxy)ethyl group is more preferred.

The "heterocyclic ring" in the formula (I) means a ring containing one to four hetero atoms such as nitrogen atom, sulfur atom or oxygen atom and includes an "5 to 14-membered aromatic heterocyclic ring" and a "5 to 10-membered non-aromatic heterocyclic ring". A preferred ring in the "heterocyclic ring" includes an aromatic heterocyclic ring such as pyrrole, pyridine, pyridazine, pyrimidine, pyrazine, pyrazole, imidazole, indole, isoindole, indolizine, purine, indazole, quinoline, isoquinoline, quinolizine, phthalazine, naphthyridine, quinoxaline, quinazoline, cinnoline, pteridine, imidazotriazine, pyrazinopyridazine, acridine, phenanthridine, carbazole, carbazoline, perimidine, phenanthroline, phenacine, thiophene, benzothiophene, furan, pyran, cyclopentapyran, benzofuran, isobenzofuran, thiazole, isothiazole, benzthiazole, benzthiadiazole, phenothiazine, isoxazole, furazane, phenoxazine, pyrazoloxazole, imidazothiazole, thienofuran, furopyrrole or pyridoxazine ring, or a non-aromatic heterocyclic ring such as pyrrolidine, pyrroline, piperidine, piperazine, imidazoline, pyrazolidine, imidazolidine, morpholine, tetrahydropyran, aziridine, oxirane, oxathiolane, phthalimide or succinimide ring. Among them, pyridine, pyridazine, pyrimidine, pyrazine, piperidine, piperazine and morpholine ring are more preferred.

The most preferred ring as the ring C in the formula (I) is benzene, pyridine, pyridazine, pyrimidine, pyrazine, piperidine, piperazine, morpholine, cyclopropane, cyclobutane, cyclopentane, cyclohexane, cycloheptane or cyclooctane ring.

The "C$_{1-6}$ alkoxy-alkoxy group" in the formula (I) means a group having the same meaning as the C$_{1-6}$ alkoxy group in the above definition to which another "C$_{1-6}$ alkoxy group" is combined and includes, for example, methoxymethoxy group, methoxyethoxy group, methoxypropoxy group, ethoxymethoxy group, ethoxyethoxy group, ethoxypropoxy group or propoxypropoxy group.

The "aryl group" in the "aryloxy group" in the formula (I) means a cyclic hydrocarbon group constituting an aromatic ring and includes, for example, a monocyclic, bicyclic or tricyclic aryl group such as phenyl group, indenyl group, naphthyl group, azulenyl group, heptalenyl group, anthryl group or phenanthrenyl group. The "aryloxy group" is preferably phenoxy group or naphthyloxy group.

The "aralkyloxy group" in the formula (I) means a group comprising oxygen atom combined with an arylalkyl group, which arylalkyl group comprises an alkyl group having one to six carbon atoms combined with a group having the same meaning as the aryl group. A preferred aralkyloxy group is, for example, benzyloxy group, phenylethoxy group, phenylpropoxy group or naphthylmethoxy group.

The "substituent" in the description of the "which may be substituted" herein includes, for example, a halogen atom, hydroxyl group, nitrile group, an alkyl group having one to six carbon atoms, a cycloalkyl group having three to eight carbon atoms, an alkoxy group having one to six carbon atoms, an C$_{1-6}$ alkoxy-alkoxy group, an aryloxy group, an aralkyloxy group, a halogenoalkyl group having one to six carbon atoms, a hydroxyalkyl group having one to six carbon atoms, a cyano-C$_{1-6}$ alkyl group, a halogenoalkoxy group having one to six carbon atoms, a hydroxyalkoxy group having one to six carbon atoms, a cyano-C$_{1-6}$ alkoxy group, an acyl group having one to six carbon atoms, nitro group, an amino group which may be substituted, an amide group which may be substituted, mercapto group or a thioalkoxy group having one to six carbon atoms, of which a halogen atom, hydroxyl group and nitrile group are preferred.

The (1-indanone)-(1,2,3,6-tetrahydropyridine) derivative, a pharmacologically acceptable salt thereof or a hydrate of them to be contained in the sigma receptor binding agent and/or acetylcholinesterase inhibitor according to the present invention is not specifically limited, and a suitable example is an (1-indanone)-(1,2,3,6-tetrahydropyridine) derivative selected from:

(1) 1-benzyl-4-[(5,6-dimethoxy-1-indanon)-2-yl]methyl-1,2,3,6-tetrahydropyridine,
(2) 1-benzyl-4-[(5,6-diethoxy-1-indanon)-2-yl]methyl-1,2,3,6-tetrahydropyridine, and
(3) 1-benzyl-4-[(5,6-diethoxy-2-fluoro-1-indanon)-2-yl]methyl-1,2,3,6-tetrahydropyridine, a pharmacologically acceptable salt thereof or a hydrate of them.

In the description of the present invention, there is the case where the structural formula of a compound represents a definite isomer. However, the present invention includes all isomers such as geometrical isomers, optical isomers based on asymmetric carbon, stereoisomers and tautomers, and mixtures thereof, is not limited by the description of the formula illustrated for the sake of convenience and can be any one isomer or a mixture thereof. Accordingly, although it is possible that an asymmetric carbon atom is present in a molecule and accordingly that optically active substance and racemic substance may be present, the present invention is not limited thereto but covers any of them. Further, crystal polymorphism may be present but, again, there is not limitation but any of single crystal form or a mixture will do. The compound or its salt related to the present invention may be an anhydride or a hydrate.

The "pharmacologically acceptable salt" in the present description is not specifically limited, as long as it can form a pharmacologically acceptable salt with the compound contained in the sigma receptor binding agent and/or acetylcholinesterase inhibitor according to the present invention, but preferred examples are a hydrohalide salt, such as hydrofluoride, hydrochloride, hydrobromide or hydroiodide; a salt of an inorganic acid, such as sulfate, nitrate, perchlorate, phosphate, carbonate or hydrogen carbonate; an organic carboxylate, such as acetate, oxalate, maleate, tartrate, fumarate or citrate; a salt of an organic sulfonic acid, such as methanesulfonate, trifluoromethanesulfonate, ethanesulfonate, benzenesulfonate, toluenesulfonate or camphorsulfonate; a salt of an amino acid, such as aspartate or glutamate; a quaternary amine salt; a salt of an alkali metal, such as sodium salt or potassium salt; or a salt of an alkaline earth metal, such as magnesium salt or calcium salt. The "pharmacologically acceptable salt" is more preferably hydrochloride or oxalate.

Production Method of (1-indanone)-(1,2,3,6-tetrahydropyridine) Derivatives

The (1-indanone)-(1,2,3,6-tetrahydropyridine) derivatives, pharmacologically acceptable salts thereof or hydrates of them according to the present invention can be prepared by various methods. A typical example thereof is as follows, but it should be noted that compounds relating to the present invention can also be prepared by any other method.

A (1-indanone)-(1,2,3,6-tetrahydropyridine) derivative represented by the formula:

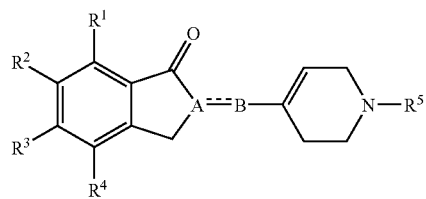

(in the formula (I), $R^1$, $R^2$, $R^3$ and $R^4$ are the same as or different from each other and each represents a group selected from hydrogen atom, a halogen atom, hydroxyl group, nitrile group, an alkyl group having one to six carbon atoms which may be substituted, a cycloalkyl group having three to eight carbon atoms which may be substituted, an alkoxy group having one to six carbon atoms which may be substituted, a cycloalkoxy group having three to eight carbon atoms which may be substituted, an acyl group having one to six carbon atoms which may be substituted, an $C_1$-$C_6$ alkoxy-carbonyl group which may be substituted, an $C_1$-$C_6$ alkyl-aminocarbonyloxy group which may be substituted, a di-($C_1$-$C_6$ alkyl)-aminocarbonyloxy group which may be substituted, nitro group, an amino group which may be substituted, an amide group which may be substituted, mercapto group and a thioalkoxy group having one to six carbon atoms which may be substituted, where $R^1$ and $R^2$, or $R^2$ and $R^3$, or $R^3$ and $R^4$ may together form an aliphatic ring, an aromatic ring, a heterocyclic ring or an alkylenedioxy ring; the partial structure:

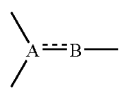

is a group represented by >C=CH—(CH$_2$)$_m$— or >C(R$^6$)—CH(R$^6$)—(CH$_2$)$_m$— (wherein m is 0 or an integer from 1 to 5; and $R^6$ is hydrogen atom, a halogen atom, hydroxyl group, an alkyl group having one to six carbon atoms, an alkoxy group having one to six carbon atoms, nitrile group, a haloalkyl group having one to six carbon atoms, a hydroxyalkyl group having one to six carbon atoms, a cyano-alkyl group having one to six carbon atoms, an aminoalkyl group having one to six carbon atoms, nitro group, azide group, an amino group which may be substituted, carbamoyl group which may be substituted, carboxyl group which may be substituted, mercapto group or a thioalkoxy group having one to six carbon atoms); and $R^5$ is hydrogen atom, an alkyl group having one to six carbon atoms which may be substituted, an alkenyl group having two to six carbon atoms which may be substituted, an alkynyl group having two to six carbon atoms which may be substituted, a cycloalkyl group having three to eight carbon atoms which may be substituted, an 2,2-(alkylenedioxy)ethyl group or a group represented by the formula:

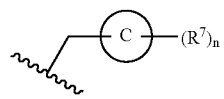

(wherein the ring C is benzene ring, an aliphatic ring or a heterocyclic ring; $R^7$s are the same as or different from each other and each represents hydrogen atom, a halogen atom, hydroxyl group, nitrile group, an alkyl group having one to six carbon atoms which may be substituted, an alkenyl group having two to six carbon atoms which may be substituted, an alkynyl group having two to six carbon atoms which may be substituted, a cycloalkyl group having three to eight carbon atoms which may be substituted, an alkoxy group having one to six carbon atoms which may be substituted, an $C_1$-$C_6$ alkoxy-alkoxy group which may be substituted, an aryloxy group which may be substituted, an aralkyloxy group which may be substituted or the like, where two of $R^7$s may together form an aliphatic ring, an aromatic ring, a heterocyclic ring or an alkylenedioxy ring); and n is an integer from 1 to 5), a pharmacologically acceptable salt thereof or a hydrate of them can be prepared, for example, by converting a pyridinium salt derivative prepared according to the method described in JP-A 8-225527, JP-A 11-263774 etc. into a 1,2,3,6-tetrahydropyridine derivative by a reduction reaction, oxidizing the product, and, where necessary, converting the oxidized product into a pharmacologically acceptable salts thereof or a hydrate of them. The reaction is represented by the following reaction scheme:

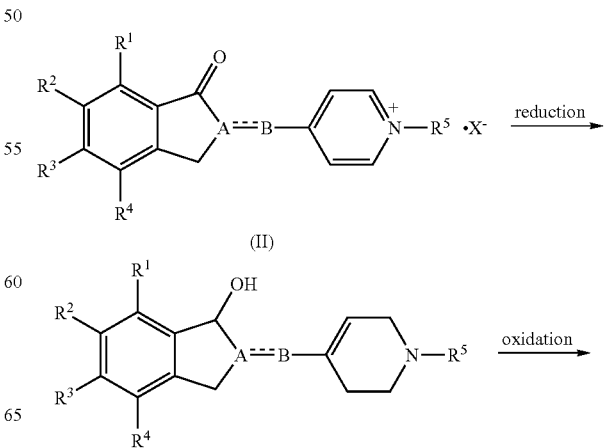

-continued

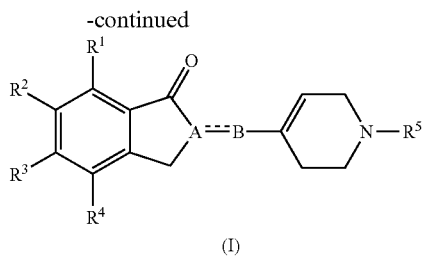

wherein $R^1$, $R^2$, $R^3$, $R^4$, $R^5$ and the partial structure:

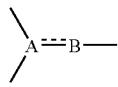

have the same meanings as defined above.

The reduction can be performed, for example, according to a procedure described in J. Med. Chem., 33, 3133(1990); J. Heterocycl. Chem., 30, 445(1993); or J. Med. Chem., 37, 151(1994). Any suitable reagent can be used as a reducing agent. Among them, a boron-containing reducing reagent is preferred, of which sodium borohydride is typically preferred. The oxidation can be performed, for example, according to a procedure described in J. Org. Chem., 55, 4767(1990); Synlett. 1991, 361; Tetrahedron, 50, 13199 (1994); J. Org. Chem., 60, 7272(1995); Synth. Commum., 27, 1643(1997); or J. Chem. Soc. Perkin Trans. 1, 1999, 3455. Any suitable reagent can be used as an oxidizing agent. Among them, manganese dioxide; a chromic acid oxidizing agent such as chromic acid-pyridine, pyridinium chlorochromate or pyridinium dichlorochromate; or a Swern oxidizing agent is preferred.

An (1-indanone)-(1,2,3,6-tetrahydropyridine) derivative represented by the formula:

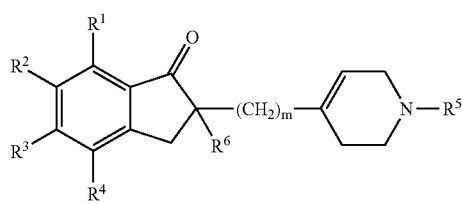

(wherein $R^1$, $R^2$, $R^3$, $R^4$, $R^5$ and m have the same meanings as defined above, provided that the case where $R^6$ is hydrogen atom is excluded, and namely, $R^6$ is a halogen atom, hydroxyl group, an alkyl group having one to six carbon atoms, an alkoxy group having one to six carbon atoms, nitrile group, a haloalkyl group having one to six carbon atoms, a hydroxyalkyl group having one to six carbon atoms, a cyano-$C_1$-$C_6$ alkyl group, an aminoalkyl group having one to six carbon atoms, nitro group, azide group, an amino group which may be substituted, carbamoyl group which may be substituted, carboxyl group which may be substituted, mercapto group or a thioalkoxy group having one to six carbon atoms), a pharmacologically acceptable salt thereof or a hydrate of them can be prepared, for example, according to a procedure described in JP-A 9-268176, JP-A 2000-319257, JP-A 2000-319258 and/or JP-A 2001-139547.

Specifically, the compound can be prepared by allowing a compound represented by the formula:

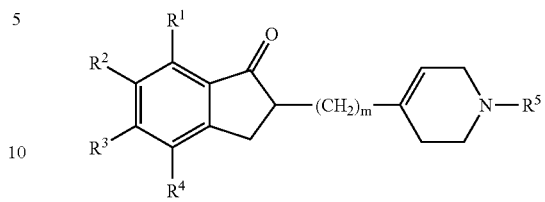

which has been prepared by the above-mentioned reaction to react with a base, allowing the reaction product to react with a corresponding electrophilic reagent, and where necessary, converting the reaction product into a pharmacologically acceptable salt thereof or a hydrate of them. The reaction is represented by the following reaction formula:

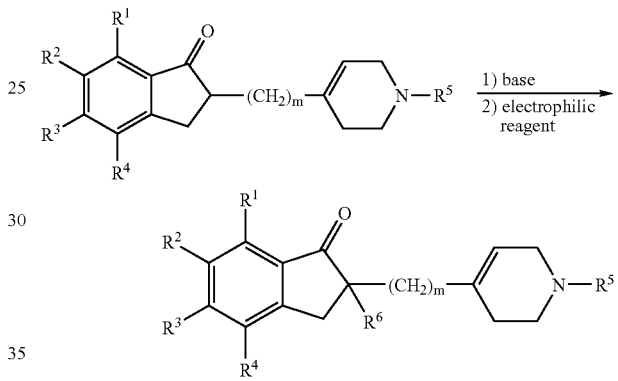

wherein $R^1$, $R^2$, $R^3$, $R^4$, $R^5$, $R^6$ and m have the same meanings as defined above, provided that the case where $R^6$ is hydrogen atom is excluded.

The base may be, but is not specifically limited to, lithium diisopropylamide (LDA) or lithium bis(trimethylsilyl) amide. The electrophilic reagent may be, but is not specifically limited to, a chlorinating reagent such as N-chlorosuccinimide; a brominating reagent such as N-bromosuccinimide; an iodizing agent such as N-iodosuccinimide; a hydroxyl-introducing reagent such as (10-camphorsulfonyl)oxaziridine; an alkyl halide such as iodomethane; an azidation reagent such as sodium azide; or a fluorinating agent. The fluorinating agent includes, for example, N-fluorobenzenesulfonimide (NFSI, CAS Registry Number (133745-75-2)), 3-cyclohexyl-2-fluoro-2,3-dihydro-3-methyl-1,1-dioxido-1,2-benzisothiazole (CMIT-F, CAS Registry Number (186806-24-6), (196106-79-3)), 2-fluoro-3,3-dimethyl-2,3-dihydro-1,2-benzisothiazole-1,1-dioxide (CAS Registry Number (124170-23-6)), diethylaminosulfur trifluoride (DAST, CAS Registry Number (38078-09-0)), N,N-diethyl-1,1,2,3,3,3-hexafluoropropylamine (Ishikawa's reagent), hydrogen fluoride, a tetraalkylammonium fluoride, potassium fluoride, cesium fluoride or hydrogen fluoride-pyridine (Olah's reagent). Among them, N-fluorobenzenesulfonimide or 3-cyclohexyl-2-fluoro-2,3-dihydro-3-methyl-1,1-dioxido-1,2-benzisothiazole is preferred.

The material compound in the reaction may form a salt or a hydrate and can be any compound that does not adversely affect the reaction. When the (1-indanone)-(1,2,3,6-tetrahydropyridine) derivative according to the present invention is obtained as a free form, it can be converted into a salt according to a conventional procedure. An isomer of the compound can be purified and isolated according to a conventional separation means such as recrystallization or chromatography. If an optically active isomer is required, it can be obtained, for example, by optical resolving a racemate or using an optically active reagent such as a fluorinating agent.

The (1-indanone)-(1,2,3,6-tetrahydropyridine) derivatives, pharmacologically acceptable salts thereof or hydrates of them relating to the present invention have a very high sigma receptor binding action and also has a very excellent acetylcholinesterase inhibitory action.

The compounds having such a sigma receptor binding action and/or an acetylcholinesterase inhibitory action relating to the present invention can be formulated into a pharmaceutical preparation according to a conventional procedure. Preferred dosage forms are tablets, coated tablets such as film-coated tablets or sugar-coated tablets, fine granules, granules, powders, capsules, syrups, troches, inhalants, suppositories, injections, ointments, eye drops, nasal drops, ear drops, cataplasms, and lotions. In the formulation, generally used fillers, disintegrators, binders, lubricants, coloring agents and flavoring agents, and if necessary, stabilizers, emulsifiers, absorption promoters, surfactants, pH adjusting agents, antiseptics, and antioxidants can be used. They can be formulated according to a conventional procedure using components generally used as raw materials for pharmaceutical preparations. Examples of such components include animal and vegetable oils such as soybean oil, beef tallow and synthetic glycerides; hydrocarbons such as liquid paraffins, squalane and solid paraffins; ester oils such as octyldodecyl myristate and isopropyl myristate; higher alcohols such as cetostearyl alcohol and behenyl alcohol; silicone resins; silicone oils; surfactants such as polyoxyethylene fatty acid esters, sorbitan fatty acid esters, glycerin fatty acid esters, polyoxyethylene sorbitan fatty acid esters, polyoxyethylene hydrogenated castor oils and polyoxyethylene-polyoxypropylene block copolymers; water-soluble polymers such as hydroxyethyl cellulose, poly (acrylic acid)s, carboxyvinyl polymers, polyethylene glycol, polyvinylpyrrolidone and methylcellulose; lower alcohols such as ethanol and isopropanol; polyhydric alcohols such as glycerol, propylene glycol, dipropylene glycol and sorbitol; sugars such as glucose and sucrose; inorganic powders such as silicic anhydride, magnesium aluminium silicate and aluminium silicate; and purified water. The fillers include, for example, lactose, corn starch, sucrose, glucose, mannitol, sorbitol, crystalline cellulose and silicon dioxide; the binders include, for example, polyvinyl alcohol, polyvinyl ether, methylcellulose, ethylcellulose, gum arabic, gum tragacanth, gelatin, shellac, hydroxypropylmethyl cellulose, hydroxypropyl cellulose, polyvinylpyrrolidone, polypropylene glycol-polyoxyethylene block polymers and meglumine; the disintegrators include, for example, starch, agar, gelatin powder, crystalline cellulose, calcium carbonate, sodium hydrogen carbonate, calcium citrate, dextrin, pectin and carboxymethylcellulose calcium; the lubricants include, for example, magnesium stearate, talc, polyethylene glycol, silica, and hardened vegetable oils; the coloring agents can be any coloring agents which are approved to add to pharmaceutical preparations; the flavoring agents include, for example, cocoa powder, menthol, aromatic powder, peppermint oil, borneol and cinnamon powder. It should be noted that the present invention is not limited to these additives.

The oral preparation is produced by mixing the compound, a salt thereof or a hydrate of them as an active ingredient with a filler, and if necessary, a binder, disintegrator, lubricant, coloring agent, flavoring agent, and other components, and formulating the mixture according to a conventional procedure into, for example, a powder, fine granules, granules, tablet, coated tablet or capsule. The tablets and granules can be appropriately coated with, for example, a sugar according to necessity. The syrups or injection preparations can be prepared according to a conventional procedure by adding a pH adjusting agent, solubilizer, and isotonizing agent, and if necessary, a solubilizing agent, stabilizer, and other components. The external preparations can be produced according to a conventional procedure not specifically limited. Base materials for use herein can be any raw materials generally used in, for example, pharmaceutical preparations (medicaments), quasi drugs and cosmetics. Such raw materials include, for example, animal and vegetable oils, mineral oils, ester oils, waxes, higher alcohols, fatty acids, silicone oils, surfactants, phospholipids, alcohols, polyhydric alcohols, water-soluble polymers, clay minerals, and purified water. Where necessary, any of pH adjusting agents, antioxidants, chelating agents, antiseptics and antimolds, coloring agents, flavors and others can be added. In addition, components having differentiation-inducing action, blood-flow accelerators, bactericides, anti-inflammatory agents, cell activators, vitamins, amino acids, humectants, keratolytic agents, and other components can be added according to necessity. The dose of the sigma receptor binding agent according to the present invention varies depending on the degree of symptom, age, sex, body weight, administration mode, type of the salt, concrete type of the disease and other factors. Generally, the agent may be administered to an adult in one to several divided doses at a daily dose of about 30 µg to about 10 g, preferably 100 µg to 5 g, and more preferably 100 µg to 100 mg for oral administration, or about 30 µg to about 1 g, preferably 100 µg to 500 mg, and more preferably 100 µg to 30 mg for injection administration.

The following sigma receptor binding assay as an example of the advantages of the present invention was performed to demonstrate the efficacy as a sigma receptor binding agent of the pharmaceutical compositions comprising the (1-indanone)-(1,2,3,6-tetrahydropyridine) derivative, a pharmacologically acceptable salt thereof or a hydrates of them relating to the present invention as an active ingredient. These compounds also have an acetylcholinesterase inhibitory action, and an example of their efficacy is also shown below. It should be noted that the use of the compounds relating to the present invention is not limited to them.

Sigma Receptor Binding Assay (1) Preparation of Receptor

The receptor was prepared by the following procedure according to the method of Weber et al. (Proc. Natl. Acad. Sci. 83, 8784-8788, 1986). Ten male guinea pigs (Crj, Hartley, from Charles River Japan, Inc.) (body weight: 234 g to 260 g) were decapitated, bled and died. The brain was immediately taken out, homogenized with 50 mM Tris-HCl (pH 7.4) in an amount ten times larger than the brain using a Teflon homogenizer and was centrifuged at a rate of 50000×g at 4° C. for 20 minutes. The washing procedure was repeated once more under the same conditions, and the resulting crude membrane fraction was subjected to the assay.

(2) Assay Method

An assay was performed using the indanone derivatives shown in Examples 2 and 3 below as a test compound and donepezil hydrochloride (1-benzyl-4-[(5,6-dimethoxy-1-indanon)-2-yl]methylpiperidine hydrochloride) as a control.

In an assay tube (Daiichi Tube, from DRL) were incubated 0.1 mL of a solution of the test compound, 0.3 mL of a 50 mM Tris-HCl buffer (pH 7.4), 0.1 mL of $^3$H-DTG solution (3.2 nM) and 0.5 mL of the receptor (guinea pig brain crude membrane fraction, 5 mg tissue) at 25° C. for 1 hour. After incubation, the mixture was filtrated using a filter paper (GF/B, from Whatman) which had been treated with 0.3% ethyleneimine. The filter paper was transferred to a vial for radioactivity measurement, mixed with 5 mL of a liquid scintillator (Atomlight, from PACKARD), and the radioactivity on the filter was determined by a liquid scintillation counter (Model 1500, from PACKARD) for 2 minutes. The specific binding and the non-specific binding in the absence of the test compound were determined in the same way as above except for using 50% DMSO solution instead of the test compound and using a 100 μM Haloperidol solution instead of the test compound, respectively.

(3) Determination of Inhibition

The inhibitions of the test compound at individual concentrations were determined from the ratio of the specific binding in the presence of the test compound to the specific binding in the absence thereof. The dose-response curve was regressed according to a logit-log model in which the ratio of the specific binding in the presence of the test compound to the specific binding in the absence thereof was subjected to logit transformation and plotted against the common logarithm value of each concentration. The $IC_{50}$, i.e., the concentration of the test compound at which the test compound inhibits 50% of binding between 3H-DTG and the guinea pig brain crude membrane fraction was determined by calculation according to the above-obtained regression equation.

The sigma receptor inhibitions ($IC_{50}$) of the compounds relating to the present invention are as follows.

TABLE 1

| Test compound | Sigma receptor inhibition $IC_{50}$ (nM) |
|---|---|
| Example 2 | 5.0 |
| Example 3 | 4.7 |
| *) Control | 18.7 |

*) Control: Donepezil hydrochloride

The results show that the present invention can provide novel sigma receptor binding agents. More specifically, they show that pharmaceutical preparations containing, as an active ingredient, the (1-indanone)-(1,2,3,6-tetrahydropyridine) derivative, a pharmacologically acceptable salt thereof or a hydrate of them according to the present invention are useful as agents for treating and/or preventing a disease in which a sigma receptor is involved and are useful as agents for treating and/or preventing a disease against which a sigma receptor antagonistic action or sigma receptor agonistic action is efficacious.

Thus, the sigma receptor binding agents according to the present invention are useful not only as antipsychotic agents but also as agents for treating or preventing a schizophrenia, depression and anxiety and agents for improving intellectual function. Further, the sigma receptor binding agents relating to the present invention are very satisfactory in adverse drug action, number of administration per certain period, and administration mode.

Inhibitory Effect on Acetylcholinesterase

Using a rat brain homogenate as a source of acetylcholinesterase, the esterase activity was determined in accordance with the method of Ellman et al (Ellman. G. L., Courtney, K. D., Andres, V. and Featherstone, R. M., Biochem.Pharmacol., 7, 88 to 95, 1961). To DTNB (5,5'-dithiobis(2-nitrobenzoic acid)), acethylthiocholine (as a substrate) and a test compound was added the rat brain homogenate and incubated. Then, the resulting yellow product produced by the reaction of the resulting thiocholine with DTNB was determined for the change in absorbance at 412 nm, to determine the acethylcholinesterase activity. The acetylcholinesterase inhibitory action of each test compound was determined in terms of 50% inhibitory concentration ($IC_{50}$).

As the test compounds, indanone derivatives according to Examples 1 and 3 were used after dissolved in distilled water or ethanol. The inhibitory action of donepezil hydrochloride (1-benzyl-4-[(5,6-dimethoxy-1-indanon)-2-yl]methylpiperidine hydrochloride) as a control was determined in the same way as above.

The acetylcholinesterase inhibitions ($IC_{50}$) of the compounds relating to the present invention are shown below.

TABLE 2

| Test compound | Acetylcholinesterase inhibition $IC_{50}$ (nM) |
|---|---|
| Example 1 | 4.2 |
| Example 3 | 0.4 |
| *) Control | 3.9 |

*) Control: Donepezil hydrochloride

These results clearly show that the pharmaceutical compositions containing, as an active ingredient, the (1-indanone)-(1,2,3,6-tetrahydropyridine) derivative, a pharmacologically acceptable salt thereof or a hydrate of them according to the present invention have an excellent acetylcholinesterase inhibitory action and are useful as agents for treating and/or preventing a disease against which an acetylcholinesterase inhibitory action is efficacious. Namely, they are also useful as agents for preventing, treating and/or improving Alzheimer-type dementia and other senile dementia, cerebrovascular dementia, an attention-deficit hyperactive disorder, glaucoma, myasthenia gravis and/or migraine.

EXAMPLES

The present invention will be illustrated in further detail with reference to the following Examples, which are not intended to limit the scope of the invention.

Example 1

Synthesis of 1-benzyl-4-[(5,6-dimethoxy-1-indanon)-2-yl]methyl-1,2,3,6-tetrahydropyridine hydrochloride

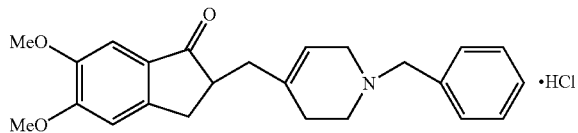

A total of 0.20 g of 1-benzyl-4-[(5,6-dimethoxy-1-indanon)-2-yl]methylpyridinium bromide prepared according to Example in JP-A 11-263774 was dissolved in 10 ml of ethanol, and 0.13 g of 90% sodium borohydride was added thereto. After stirring at room temperature for 2 hours, the mixture was adjusted to pH 6 to 7 by acetic acid under ice-cooling, and then evaporated. The residue was extracted with ethyl acetate and a saturated aqueous solution of sodium carbonate. The organic layer was washed with brine, dried over magnesium sulfate ($MgSO_4$), and then evaporated. The resulting residue was purified by preparative thin layer silica gel column chromatography (methylene chloride/methanol system), to give 90 mg of a pale yellow oil.

This oil was dissolved in 6 ml of methylene chloride, and 0.45 g of manganese dioxide was added. After stirring for 2 hours, 0.45 g of manganese dioxide was further added, and the mixture was stirred overnight. The solid substance was filtered off, and then the filtrate was evaporated. The residue was purified by preparative thin layer silica gel column chromatography (methylene chloride/methanol system), to give 41 mg of a free form of the title compound as a pale yellow oil (total yield in two steps: 25%).

$^1$H-NMR (400 Mz:$CDCl_3$) δ: 1.96-2.23 (3H, m), 2.59 (2H, bt, J=5.6 Hz), 2.65-2.87 (3H, m), 3.00 (2H, bs), 3.18 (1H, dd, J=7.2 Hz, J=17.2 Hz), 3.60 (2H, s), 3.91 (3H, s), 3.97 (3H, s), 5.44 (1H, bs), 6.86 (1H, s), 7.18 (1H, s), 7.24-7.38 (5H, m).

This oil was converted into a hydrochloride according to a conventional procedure and was recrystallized from ethanol/t-butyl methyl ether, to give the title compound as pale yellowish white crystals.

ESI-MS : m/z=378 (M+H$^+$).

Example 2

Synthesis of 1-benzyl-4-[(5,6-diethoxy-1-indanon)-2-yl]methyl-1,2,3,6-tetrahydropyridine hydrochloride

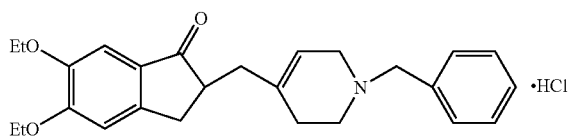

The free form of the title compound was obtained as a pale yellow oil in the same way as Example 1 (total yield in two steps: 43%).

$^1$H-NMR (400 Mz:$CDCl_3$) δ: 1.46 (3H, t, J=6.8 Hz), 1.51 (3H, t, J=6.8 Hz), 1.95-2.22 (3H, m), 2.52-2.84 (3H, m), 3.15 (1H, dd, J=7.2 Hz, J=17.2 Hz), 3.59 (2H, s), 4.11 (2H, q, J=6.8 Hz), 4.17 (2H, q, J=6.8 Hz), 5.43 (1H, bs), 6.83 (1H, s), 7.16 (1H, s), 7.24-7.37 (5H, m).

This oil was converted into a hydrochloride according to a conventional procedure and was recrystallized from ethanol/t-butyl methyl ether, to give the title compound as pale yellowish white crystals.

ESI-MS: m/z=406 (M+H$^+$).

Example 3

Synthesis of 1-benzyl-4-[(5,6-diethoxy-2-fluoro-1-indanon)-2-yl]methyl-1,2,3,6-tetrahydropyridine hydrochloride

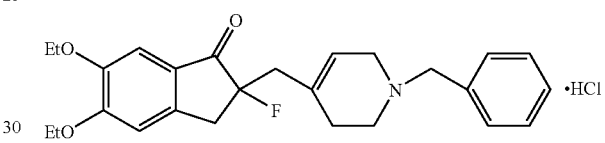

The following reactions were performed under nitrogen atmosphere.

A total of 0.30 g of 1-benzyl-4-[(5,6-diethoxy-1-indanon)-2-yl]methyl-1,2,3,6-tetrahydropyridine was dissolved in 10 ml of tetrahydrofuran (THF), was cooled to −78° C., and 1.11 ml of 1.0 M THF solution of lithium bis(trimethylsilyl)amide was injected thereinto. The mixture was raised in temperature from −78° C. to −10° C. over 30 minutes, was then cooled again to −78° C., and a solution of 0.35 g of N-fluorobenzenesulfonimide in 5 ml of THF was added. The mixture was gradually raised in temperature from −78° C. to room temperature, was stirred overnight, was treated with a saturated aqueous solution of ammonium chloride, and was extracted with ethyl acetate. The organic layer was washed with brine, dried over magnesium sulfate ($MgSO_4$), and then evaporated. The resulting residue was purified by silica gel column chromatography (NH-silica gel; n-hexane/ethyl acetate system), to give 0.24 g (77%) of a free form of the title compound as a pale yellow oil.

$^1$H-NMR (400 Mz: $CDCl_3$) δ:1.47 (3H, t, J=6.8 Hz), 1.52 (3H, t, J=6.8 Hz), 2.03-2.58 (5H, m), 2.76 (1H, t, J=14.4 Hz), 2.90-3.03 (2H, m), 3.17 (1H, dd, J=17.6 Hz, J=22.4 Hz), 3.39 (1H, dd, J=11.2 Hz, J=17.6 Hz), 3.55 (2H, s), 4.10 (2H, q, J=6.8 Hz), 4.18 (2H, q, J=6.8 Hz), 5.48 (1H, bs), 6.80 (1H, s), 7.18 (1H, s), 7.22-7.34 (5H, m).

This oil was converted into a hydrochloride according to a conventional procedure and was recrystallized from ethanol/t-butyl methyl ether, to give the title compound as pale yellowish white crystals.

ESI-MS : m/z=424 (M+H$^+$).

The invention claimed is:

1. An (1-indanone)-(1,2,3,6-tetrahydropyridine) compound represented by the formula:

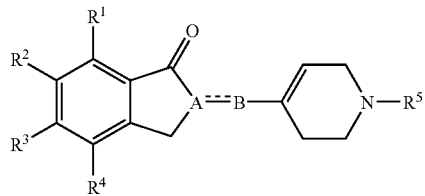

(In the formula (I), $R^1$, $R^2$, $R^3$ and $R^4$ are the same as or different from each other and each represents a group selected from hydrogen atom, a halogen atom, hydroxyl group, nitrile group, an alkyl group having one to six carbon atoms which may be substituted, a cycloalkyl group having three to eight carbon atoms which may be substituted, an alkoxy group having one to six carbon atoms which may be substituted, a cycloalkoxy group having three to eight carbon atoms which may be substituted, an acyl group having one to six carbon atoms which may be substituted, an $C_1$-$C_6$ alkoxy-carbonyl group which may be substituted, an $C_1$-$C_6$ alkyl-aminocarbonyloxy group which may be substituted, a di-($C_1$-$C_6$ alkyl)-aminocarbonyloxy group which may be substituted, nitro group, an amino group which may be substituted, an amide group which may be substituted, mercapto group and a thioalkoxy group having one to six carbon atoms which may be substituted, where $R^1$ and $R^2$, or $R^2$ and $R^3$, or $R^3$ and $R^4$ may together form an aliphatic ring, an aromatic ring, a heterocyclic ring or an alkylenedioxy ring; the partial structure;

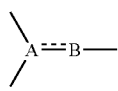

is a group represented by >C=CH—(CH$_2$)$_m$— or >C(R$^6$)—CH(R$^6$)—(CH$_2$)$_m$— (wherein m is 0 or an integer from 1 to 5; and $R^6$ is hydrogen atom, a halogen atom, hydroxyl group, an alkyl group having one to six carbon atoms, an alkoxy group having one to six carbon atoms, nitrile group, a haloalkyl group having one to six carbon atoms, a hydroxyalkyl group having one to six carbon atoms, a cyano-$C_1$-$C_6$ alkyl group, an aminoalkyl group having one to six carbon atoms, nitro group, azide group, an amino group which may be substituted, carbamoyl group which may be substituted, carboxyl group which may be substituted, mercapto group or a thioalkoxy group having one to six carbon atoms); and $R^5$ is hydrogen atom, an alkyl group having one to six carbon atoms which may be substituted, an alkenyl group having two to six carbon atoms which may be substituted, an alkynyl group having two to six carbon atoms which may be substituted, a cycloalkyl group having three to eight carbon atoms which may be substituted, an 2,2-(alkylenedioxy)ethyl group or a group represented by the formula:

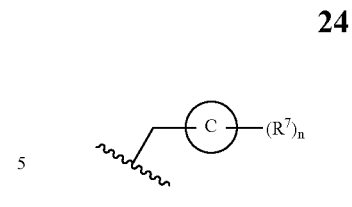

(wherein the ring C is benzene ring, an aliphatic ring or a heterocyclic ring; $R^7$s are the same as or different from each other and each represents hydrogen atom, a halogen atom, hydroxyl group, nitrile group, an alkyl group having one to six carbon atoms which may be substituted, an alkenyl group having two to six carbon atoms which may be substituted, an alkynyl group having two to six carbon atoms which may be substituted, a cycloalkyl group having three to eight carbon atoms which may be substituted, an alkoxy group having one to six carbon atoms which may be substituted, an $C_1$-$C_6$ alkoxy-alkoxy group which may be substituted, an aryloxy group which may be substituted, an aralkyloxy group which may be substituted or the like, where two of $R^7$s may together form an aliphatic ring, an aromatic ring, a heterocyclic ring or an alkylenedioxy ring; and n is an integer from 1 to 5)), a pharmacologically acceptable salt thereof or a hydrate of them.

2. The (1-indanone)-(1,2,3,6-tetrahydropyridine) compound according to claim 1, a pharmacologically acceptable salt thereof or a hydrate of them, wherein $R^1$ and $R^4$ are hydrogen atoms; and $R^2$ and $R^3$ are the same as or different from each other and each represents hydrogen atom, a halogen atom, an alkyl group having one to six carbon atoms which may be substituted, a cycloalkyl group having three to eight carbon atoms which may be substituted, an alkoxy group having one to six carbon atoms which may be substituted or a cycloalkoxy group having three to eight carbon atoms which may be substituted, or $R^2$ and $R^3$ may together form an aliphatic ring, an aromatic ring, a heterocyclic ring or an alkylenedioxy ring.

3. The (1-indanone)-(1,2,3,6-tetrahydropyridine) compound according to claim 1 or 2, a pharmacologically acceptable salt thereof or a hydrate of them, wherein $R^6$ is hydrogen atom, a halogen atom or an alkyl group having one to six carbon atoms.

4. The (1-indanone)-(1,2,3,6-tetrahydropyridine) compound according to claim 1, a pharmacologically acceptable salt thereof or a hydrate of them, wherein $R^5$ is a group represented by the formula:

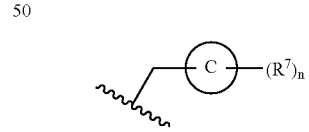

wherein the ring C, $R^7$ and n have the same meanings as defined above.

5. The (1-indanone)-(1,2,3,6-tetrahydropyridine) compound according to claim 4, a pharmacologically acceptable salt thereof or a hydrate of them, wherein the ring C is benzene ring or a cycloalkyl ring having three to eight carbon atoms.

6. The (1-indanone)-(1,2,3,6-tetrahydropyridine) compound according to claim 4, a pharmacologically acceptable salt thereof or a hydrate of them, wherein $R^7$s are the same as or different from each other and each represents hydrogen atom, a halogen atom, an alkyl group having one to six carbon atoms which may be substituted, an alkenyl group having two to six carbon atoms which may be substituted, an alkynyl group having two to six carbon atoms which may be substituted, a cycloalkyl group having three to eight carbon atoms which may be substituted, or two of $R^7$s may together form an aliphatic ring, an aromatic ring, a heterocyclic ring or an alkylenedioxy ring.

7. The (1-indanone)-(1,2,3,6-tetrahydropyridine) compound according to claim 4, a pharmacologically acceptable salt thereof or a hydrate of them, wherein n is an integer of 1 or 2.

8. The (1-indanone)-(1,2,3,6-tetrahydropyridine) compound according to claim 1, a pharmacologically acceptable salt thereof or a hydrate of them, wherein the partial structure:

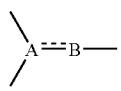

is a group represented by $>C(R^6)$—$CH(R^6)$—$(CH_2)_m$— (wherein m is 0 or an integer from 1 to 5; and $R^6$ is hydrogen atom).

9. The (1-indanone)-(1,2,3,6-tetrahydropyridine) compound according to claim 1, a pharmacologically acceptable salt thereof or a hydrate of them, wherein the partial structure:

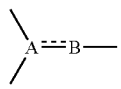

is a group represented by $>C(R^6)$—$CH(R^6)$—$(CH_2)_m$— (wherein m is 0 or an integer from 1 to 5; and $R^6$ is a halogen atom, hydroxyl group, an alkyl group having one to six carbon atoms, an alkoxy group having one to six carbon atoms, nitrile group, a haloalkyl group having one to six carbon atoms, a hydroxyalkyl group having one to six carbon atoms, a cyano-$C_1$-$C_6$ alkyl group, an aminoalkyl group having one to six carbon atoms, nitro group, azide group, an amino group which may be substituted, carbamoyl group which may be substituted, carboxyl group which may be substituted, mercapto group or a thioalkoxy group having one to six carbon atoms.

10. The (1-indanone)-(1,2,3,6-tetrahydropyridine) compound according to claim 1, a pharmacologically acceptable salt thereof or a hydrate of them, wherein the (1-indanone)-(1,2,3,6-tetrahydropyridine) compound represented by the formula (I) is one selected from:

(1) 1-benzyl-4-[(5,6-dimethoxy-1-indanon)-2-yl]methyl-1,2,3,6-tetrahydropyridine, (2) 1-benzyl-4-[(5,6-diethoxy-1-indanon)-2-yl]methyl-1,2,3,6-tetrahydropyridine, and (3) 1-benzyl-4-[(5,6-diethoxy-2-fluoro-1-indanon)-2-yl]methyl-1,2,3,6-tetrahydropyridine.

11. A pharmaceutical composition comprising the (1-indanone)-(1,2,3,6-tetrahydropyridine) compound according to claim 1, a pharmacologically acceptable salt thereof or a hydrate of them.

12. The pharmaceutical composition according to claim 11, which is a sigma receptor binding agent.

13. The pharmaceutical composition according to claim 11, which is a sigma receptor antagonist or a sigma receptor agonist.

14. The pharmaceutical composition according to claim 11, which is an agent for preventing, treating and/or improving a disease against which a sigma receptor-active drug is efficacious.

15. The pharmaceutical composition according to claim 11, which is an agent for preventing, treating and/or improving a disease against which a sigma receptor antagonistic action is efficacious.

16. The pharmaceutical composition according to claim 11, which is an agent for preventing, treating and/or improving a disease against which a sigma receptor agonistic action is efficacious.

17. The pharmaceutical composition according to claim 11, which is an agent for preventing, treating and/or improving a mental disorder.

18. The pharmaceutical composition according to claim 17, wherein the mental disorder is at least one selected from a disorder accompanied with cerebrovascular dementia and/or senile dementia, a schizophrenic disorder, an emotional disturbance, a depression, a neurosis, a psychophysiologic disorder and an anxiety disorder.

19. The pharmaceutical composition according to claim 18, wherein the disorder accompanied with cerebrovascular dementia and/or senile dementia is at least one selected from aggressive behavior, mental excitement, wandering, delirium, hallucination and hyperkinesis.

20. The pharmaceutical composition according to claim 11, which is an agent for improving intellectual function.

21. The pharmaceutical composition according to claim 11, which is an acetylcholinesterase inhibitor.

22. The pharmaceutical composition according to claim 11, which is an agent for preventing, treating and/or improving senile dementia, cerebrovascular dementia, an attention-deficit hyperactive disorder, glaucoma, myasthenia gravis and/or migraine.

23. The pharmaceutical composition according to claim 21, wherein the senile dementia is an Alzheimer-type dementia.

24. A method for preparing the (1-indanone)-(1,2,3,6-tetrahydropyridine) compound of claim 8, a pharmacologically acceptable salt thereof or a hydrate of them, which comprises reducing an (1-indanone)-pyridinium compound represented by the formula:

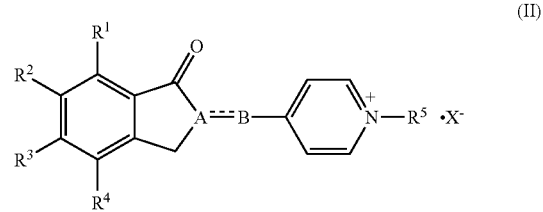

(in the formula (II), $R^1$, $R^2$, $R^3$ and $R^4$ are the same as or different from each other and each represents a group selected from hydrogen atom, a halogen atom, hydroxyl group, nitrile group, an alkyl group having one to six carbon atoms which may be substituted, a cycloalkyl group having three to eight carbon atoms which may be substituted, an alkoxy group having one to six carbon atoms which may be substituted, a cycloalkoxy group having three to eight carbon atoms which may be substituted, an acyl group having one to six carbon atoms which may be substituted, an $C_1$-$C_6$ alkoxy-carbonyl group which may be substituted, an $C_1$-$C_6$ alkyl-aminocarbonyloxy group which may be substituted, a di-($C_1$-$C_6$ alkyl)-aminocarbonyloxy group which may be substituted, nitro group, an amino group which may be substituted, an amide group which may be substituted, mercapto group and a thioalkoxy group having one to six carbon atoms which may be substituted, where $R^1$ and $R^2$, or $R^2$ and $R^3$, or $R^3$ and $R^4$ may together form an aliphatic ring, an aromatic ring, a heterocyclic ring or an alkylenedioxy ring; the partial structure:

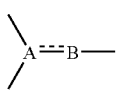

is a group represented by >C=CH—$(CH_2)_m$— or >C($R^6$)—CH($R^6$)—$(CH_2)_m$— wherein m is 0 or an integer from 1 to 5; and $R^6$ is hydrogen atom); and $R^5$ is hydrogen atom, an alkyl group having one to six carbon atoms which may be substituted, an alkenyl group having two to six carbon atoms which may be substituted, an alkynyl group having two to six carbon atoms which may be substituted, a cycloalkyl group having three to eight carbon atoms which may be substituted, an 2,2-(alkylenedioxy)ethyl group or a group represented by the formula:

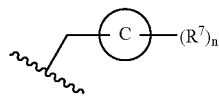

(wherein the ring C is benzene ring, an aliphatic ring or a heterocyclic ring; $R^7$s are the same as or different from each other and each represents hydrogen atom, a halogen atom, hydroxyl group, nitrile group, an alkyl group having one to six carbon atoms which may be substituted, an alkenyl group having two to six carbon atoms which may be substituted, an alkynyl group having two to six carbon atoms which may be substituted, a cycloalkyl group having three to eight carbon atoms which may be substituted, an alkoxy group having one to six carbon atoms which may be substituted, an $C_1$-$C_6$ alkoxy-alkoxy group which may be substituted, an aryloxy group which may be substituted, an aralkyloxy group which may be substituted or the like, where two of $R^7$s may together form an aliphatic ring, an aromatic ring, a heterocyclic ring or an alkylenedioxy ring; and n is an integer from 1 to 5), a pharmacologically acceptable salt thereof or a hydrate of them with a reducing agent and oxidizing the reduced product with an oxidizing agent.

25. The method for preparing the (1-indanone)-(1,2,3,6-tetrahydropyridine) compound, a pharmacologically acceptable salt thereof or a hydrate of them according to claim 24, wherein the reducing agent is sodium borohydride, and wherein the oxidizing agent is manganese dioxide, a chromium oxidizing agent or a Swern oxidizing agent.

26. A method for preparing the (1-indanone)-(1,2,3,6-tetrahydropyridine) compound of claim 9, a pharmacologically acceptable salt thereof or a hydrate of them, which comprises allowing the (1-indanone)-(1,2,3,6-tetrahydropyridine) compound of claim 8, a pharmacologically acceptable salt thereof or a hydrate of them to react with a base, and subjecting the reaction product to an electrophilic reaction with an electrophilic reagent.

27. The method for preparing the (1-indanone)-(1,2,3,6-tetrahydropyridine), a pharmacologically acceptable salt thereof or a hydrate of them according to claim 26, wherein the base is lithium diisopropylamide (LDA) or lithium bis(trimethylsilyl)amide.

28. The method for preparing the (1-indanone)-(1,2,3,6-tetrahydropyridine), a pharmacologically acceptable salt thereof or a hydrate of them according to claim 26, wherein the electrophilic reagent is N-chlorosuccinimide, N-bromosuccinimide, N-iodosuccinimide, (10-camphorsulfonyl)oxaziridine, iodomethane or sodium azide.

29. The method for preparing the (1-indanone)-(1,2,3,6-tetrahydropyridine), a pharmacologically acceptable salt thereof or a hydrate of them according to claim 26, wherein the electrophilic reagent is a fluorinating agent.

30. The method for preparing the (1-indanone)-(1,2,3,6-tetrahydropyridine), a pharmacologically acceptable salt thereof or a hydrate of them according to claim 29, wherein the fluorinating agent is N-fluorobenzenesulfonimide, 3-cyclohexyl-2-fluoro-2,3-dihydro-3-methyl-1,1-dioxido-1,2-benzisothiazole, 2-fluoro-3,3-dimethyl-2,3-dihydro-1,2-benzisothiazole-1,1-dioxide, diethylaminosulfur trifluoride, N,N-diethyl-1,1,2,3,3,3-hexafluoropropylamine, hydrogen fluoride, a tetraalkylammonium fluoride, potassium fluoride, cesium fluoride or hydrogen fluoride-pyridine.

* * * * *